United States Patent
Lafontaine

(10) Patent No.: US 6,709,431 B2
(45) Date of Patent: Mar. 23, 2004

(54) CRYO-TEMPERATURE MONITORING

(75) Inventor: Daniel M. Lafontaine, Plymouth, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 10/024,899

(22) Filed: Dec. 18, 2001

(65) Prior Publication Data

US 2003/0114843 A1 Jun. 19, 2003

(51) Int. Cl.$^7$ .............................................. A61B 18/18
(52) U.S. Cl. .................................... 606/21; 606/20
(58) Field of Search .................... 606/20–26; 600/549

(56) References Cited

U.S. PATENT DOCUMENTS

| | | |
|---|---|---|
| 3,125,096 A | 3/1964 | Antiles et al. |
| 4,784,133 A | 11/1988 | Mackin |
| 4,860,744 A | 8/1989 | Johnson et al. |
| 5,019,042 A | 5/1991 | Sahota |
| 5,057,106 A | 10/1991 | Kasevich et al. |
| 5,078,713 A | 1/1992 | Varney |
| 5,108,390 A | 4/1992 | Potocky et al. |
| 5,139,496 A | 8/1992 | Hed |
| 5,147,355 A | 9/1992 | Friedman et al. |

(List continued on next page.)

FOREIGN PATENT DOCUMENTS

| | | |
|---|---|---|
| DE | 197 24 082 A1 | 12/1998 |
| FR | 2 403 063 | 4/1979 |
| GB | 1019028 | 2/1966 |
| WO | WO 0047118 | 8/2000 |
| WO | WO 00/47118 | 8/2000 |
| WO | WO 00/47121 | 8/2000 |
| WO | WO 01/22897 | 4/2001 |

OTHER PUBLICATIONS

A. Schilling et al., "Nature of the Vehicle for Cryopreservation of Human Peripheral Veins: Preservation of Reactivity to Pharmacological Stimuli", Cryobiology 32, 109–113 (1995).

P. Nataf et al., "Effect of Cold Anoxia and Cryopreservation on Metabolic and Contractile Functions of Human Mammary Artery", Cryobiology, 32, 327–333 (1995).

Mazur, P., Physical–Chemical Factors Underlying Cell Injury in Cryosurgical Freezing, Cryosurgery, pp. 32–51, published on date even with or prior to Jan. 12, 1999.

Cahan, W., "Five Years of Cryosurgical Experience: Benign and Malignant Tumors with Hemorrhagic Conditions", Cryosurgery, pp. 388–391, published on date even with or prior to Jan. 12, 1999.

Zacarian, S., "Cryosurgery of Tumors of the Skin and Oral Cavity", 5 pages, published on date even with or prior to Jan. 12, 1999.

B. Fuller et al., "Clinical Applications of Cryobiology", 4 pages, published on date even with or prior to Jan. 12, 1999.

G. Morris et al., "Effects of Low Temperatures on Biological Membranes", 2 pages, published on date even with or prior to Jan. 12, 1999.

R. Coger et al., "Preservation Techniques for Biomaterials", The Biomedical Engineering Handbook, 8 pages, 1995.

(List continued on next page.)

Primary Examiner—Michael Peffley
Assistant Examiner—Peter Vrettakos
(74) Attorney, Agent, or Firm—Fish & Richardson, P.C., P.A.

(57) ABSTRACT

Devices and methods for cold-treating lesions within the body. A temperature monitoring device for use with a cryo therapy apparatus may include a cryo therapy apparatus, one or more tubular members coupled to the cryo therapy apparatus, and a temperature monitoring member coupled to the tubular member. The temperature monitoring member may comprise a retractable needle, an infrared sensor, an ultrasound transmitter, or a stent having a plurality of spikes.

21 Claims, 3 Drawing Sheets

U.S. PATENT DOCUMENTS

| | | |
|---|---|---|
| 5,190,540 A | 3/1993 | Lee |
| 5,220,927 A | 6/1993 | Astrahan et al. |
| 5,281,215 A | 1/1994 | Milder |
| 5,334,181 A | 8/1994 | Rubinsky et al. |
| 5,334,193 A | 8/1994 | Nardella |
| 5,335,669 A | 8/1994 | Tilson et al. |
| 5,342,301 A | 8/1994 | Saab |
| 5,417,689 A | 5/1995 | Fine |
| 5,423,807 A | 6/1995 | Milder |
| 5,443,470 A | 8/1995 | Stern et al. |
| 5,454,807 A | 10/1995 | Lennox et al. |
| 5,501,681 A | 3/1996 | Neuwirth et al. |
| 5,520,682 A | 5/1996 | Baust et al. |
| 5,536,252 A | 7/1996 | Imran et al. |
| 5,562,720 A | 10/1996 | Stern et al. |
| 5,624,392 A * | 4/1997 | Saab .................. 604/43 |
| 5,674,218 A | 10/1997 | Rubinsky et al. |
| 5,733,319 A * | 3/1998 | Neilson et al. .............. 607/105 |
| 5,807,391 A | 9/1998 | Wijkamp |
| 5,868,735 A | 2/1999 | Lafontaine |
| 5,957,917 A | 9/1999 | Dolron et al. |
| 5,971,979 A * | 10/1999 | Joye et al. ................... 606/21 |
| 6,012,457 A | 1/2000 | Lesh |
| 6,024,740 A | 2/2000 | Lesh et al. |
| 6,190,378 B1 * | 2/2001 | Jarvinen ...................... 606/21 |
| 6,193,644 B1 | 2/2001 | Dobak, III et al. |
| 6,283,959 B1 | 9/2001 | Lalonde et al. |
| 6,290,696 B1 | 9/2001 | Lafontaine |
| 6,355,029 B1 * | 3/2002 | Joye et al. ................... 606/21 |
| 6,405,732 B1 * | 6/2002 | Edwards et al. ............ 128/898 |

OTHER PUBLICATIONS

C. Hunt et al., "Fractures in Cryopreserved Arteries", *Cryobiology*, 31, 506–515 (1994).

Article entitled "Prostate Cryosurgery now Reimbursable in Southern California", *Healthcare Technology Management*, published on date even with or prior to Jan. 12, 1999, 1 page.

Abstract entitled "Renal Cryoablation in a Canine Model", *Urology*, May 1996, 1 page.

Abstract entitled "Cox Maze Operation Without Cryoablation for the Treatment of Chronic Atrial Fibrillation", *Annals of Thoracic Surgery*, Aug. 1995, 1 page.

Abstract entitled "Percutaneous Serial Catheterization in Swine: a Practical Approach", *Journal of Investigative Surgery*, Mar.–Apr. 1995, 1 page.

Abstract entitled "Cardiac Rhythm Disturbances due to Caval Occlusion During Hepatic Cryosurgery", *Cryobiology*, Oct. 1994, 1 page.

Abstract entitled "Intractable Chest Pain in Cardiomyopathy: Treatment by a Novel Technique of Cardiac . . . ", *British Heart Journal*, Dec. 1993, 1 page.

Abstract entitled "Histologic Study of Chronic Catheter Cryoablation of Atrioventricular Conduction in Swine" *American Heart Journal*, Jun. 1993, 1 page.

Abstract entitled "Argon Beam Coagulation Compared with Cryoablation of Ventricular Subendocardium", *Annals of Thoracic Surgery*, Jan. 1993, 1 page.

* cited by examiner

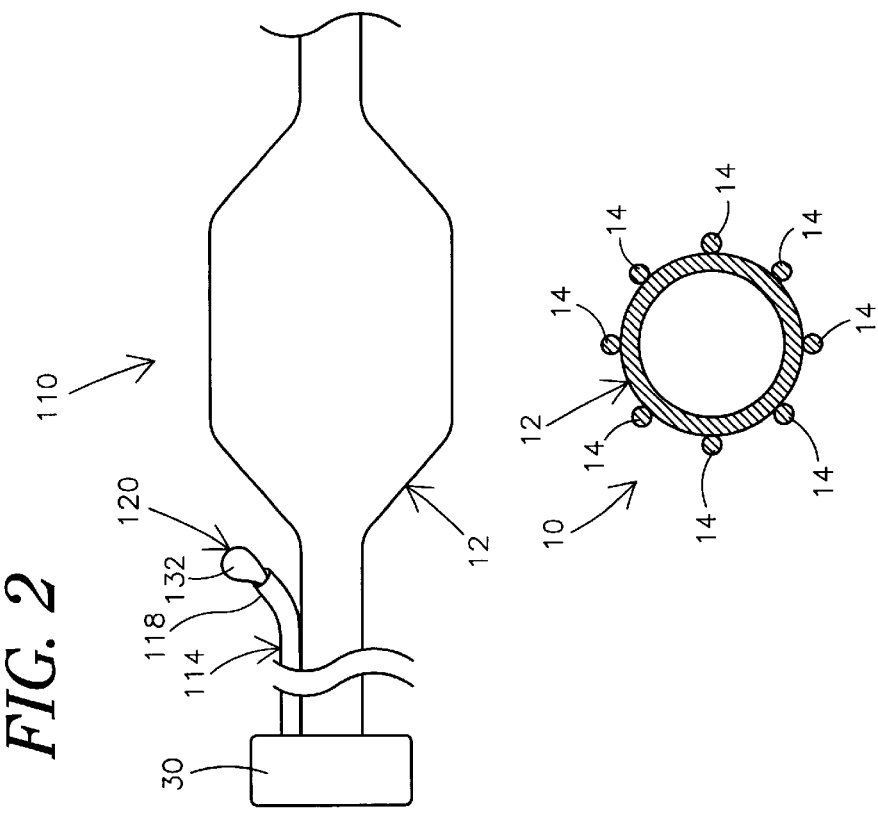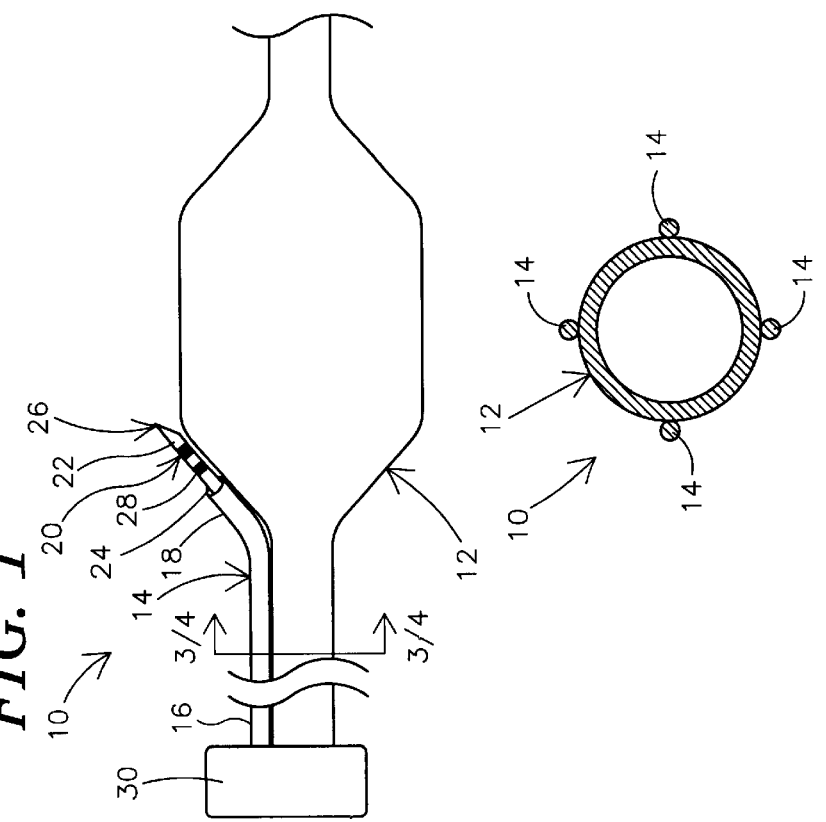

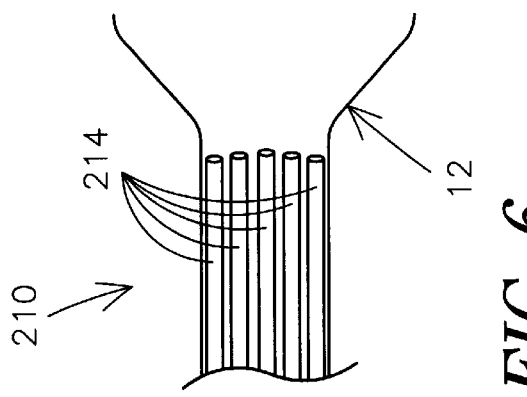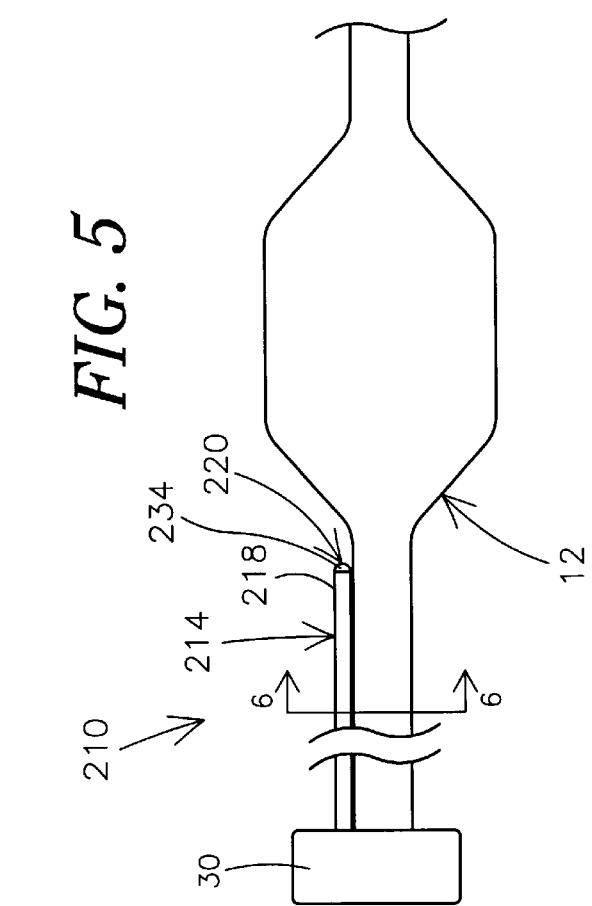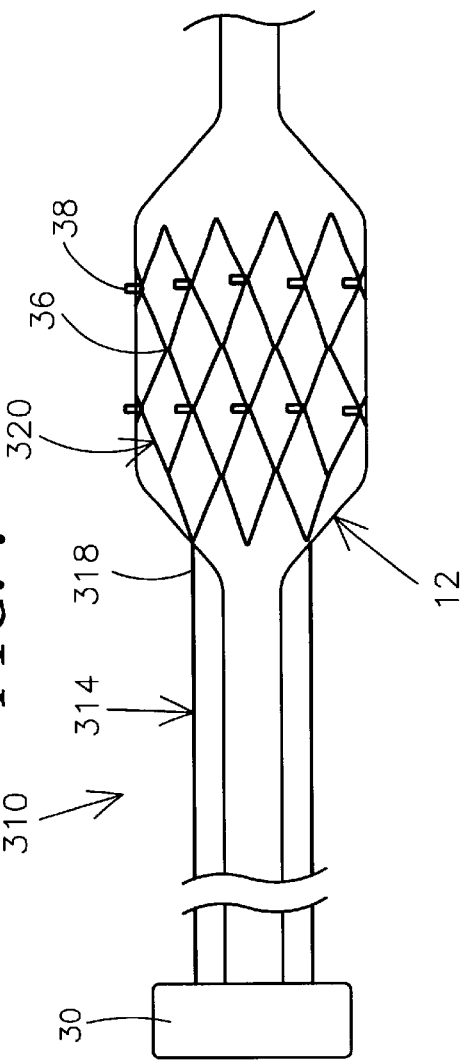

CRYO-TEMPERATURE MONITORING

BACKGROUND OF THE INVENTION

1. Field of the Invention

The present invention pertains generally to the field of cryo therapy. More particularly, the present invention pertains to cryo balloon therapy catheters for use in causing cold-induced necrosis.

2. Description of the Related Art

A number of medical conditions may be treated using ablative techniques or devices. Ablative techniques, generally, result in the necrosis of abnormal tissue at an area of interest. Ablation of the abnormal tissue may result in an efficacious treatment for a medical condition. For example, atrial fibrillation may be the result of abnormal electrical activity in the left atrium and the pulmonary vein, and may be treatable by ablation of the abnormal tissue within the left atrium and/or the pulmonary vein.

Atrial fibrillation is a serious medical condition that is the result of abnormal electrical activity within the heart. This abnormal activity may occur at regions of the heart including the sino-atrial (SA) node, the atriovenricular (AV) node, the bundle of His, or within other areas of cardiac tissue. Moreover, atrial fibrillation may be caused by abnormal activity within a isolated focal center within the heart. It is believed that these foci can originate within the pulmonary vein, particularly the superior pulmonary veins.

Minimally invasive techniques have been described that use ablation catheters to target the pulmonary vein with the hope of ablating foci having abnormal electrical activity. The techniques typically are characterized by application of energy to cause lesions within the foci or other areas possessing abnormal electrical activity.

Some ablation devices utilize radio frequency (RF) energy for ablation, including the device disclosed in U.S. Pat. No. 6,024,740 to Lesh et al. The RF energy devices may be used to ablate an area of interest with heat. The use of RF energy for ablation may, however, lead to untoward healing responses such as collagen build up at the area of interest after treatment. Moreover, RF ablation of within an atrium may decrease atrial output. A need, therefore, exists for ablative devices and methods that include improved healing responses.

An alternative treatment strategy has been developed that uses cooling energy for. ablation. This method, termed cryoplasty or cryo balloon therapy, may be used to cool the lesion to freeze a portion of the affected area. For example, cryo balloon therapy may be used to freeze a lesion within a blood vessel that might otherwise lead to restenosis or recoil.

In addition to its potential utility in preventing and slowing restenosis and addressing recoil, cryo balloon therapy may be used for ablation techniques. For example, cryo balloon therapy may be efficacious in varicose vein treatment of incompetent valves, valvular disease, mitral valve regurgitation therapy, atrial fibrillation, gastric reflux disease, gastro esophageal reflux disease, GURD, esophageal disease, cancer treatment including stomach or uterine cancer, etc.

Uses of cryo balloon therapy include cold-induced necrosis of cells within the body. When the target area is located within the heart or pulmonary vasculature, it may be important to precisely control the cryo balloon therapy catheter to necrosis only the desired tissue. Precise temperature regulation may be required to necrosis target tissues while minimizing damage to healthy tissue. Moreover, precise temperature monitoring may be useful in target areas that have an uneven surface, such as trabeculae within the heart. A need, therefore, exists for cryoplasty catheters with precise temperature monitoring capabilities.

BRIEF SUMMARY OF THE INVENTION

The present invention pertains to a refinement to cryo therapy catheters that may incorporate some of the needs described above. More particularly, the present invention comprises a temperature monitoring device for use with a cryo balloon therapy catheters. The temperature monitoring device may be coupled to a cryo therapy catheter and may be used to measure temperature while performing a medical procedure, for example cryo balloon therapy or cryoplasty. The temperature monitoring device may comprise a tubular member having a temperature monitoring member coupled thereto.

The temperature monitoring member may comprise a retractable needle slidably disposed within a lumen of the tubular member. Alternatively, the temperature monitoring member comprises an infrared optic sensor, an ultrasound transmitter, or a sheath that encircles the cryo therapy apparatus having a plurality of thermal spikes. In addition, one or more tubular members may be disposed about the cryo therapy apparatus in an array.

BRIEF DESCRIPTION OF THE SEVERAL VIEWS OF THE DRAWINGS

FIG. 1 is a plan view of a cryo therapy apparatus including a retractable needle;

FIG. 2 is an alternate cryo therapy apparatus including an infrared sensor;

FIG. 3 is a cross-sectional view of a quartet array arrangement of tubular members;

FIG. 4 is a cross-sectional view of an octet array arrangement of tubular members;

FIG. 5 is a second alternate embodiment of a cryo therapy apparatus including an ultrasound transmitter;

FIG. 6 is a detailed view of an arrangement of the tubular members shown in FIG. 5;

FIG. 7 is a third alternate embodiment of a cryo therapy apparatus including a plurality of thermal spikes;

DETAILED DESCRIPTION OF THE INVENTION

Figure 8:
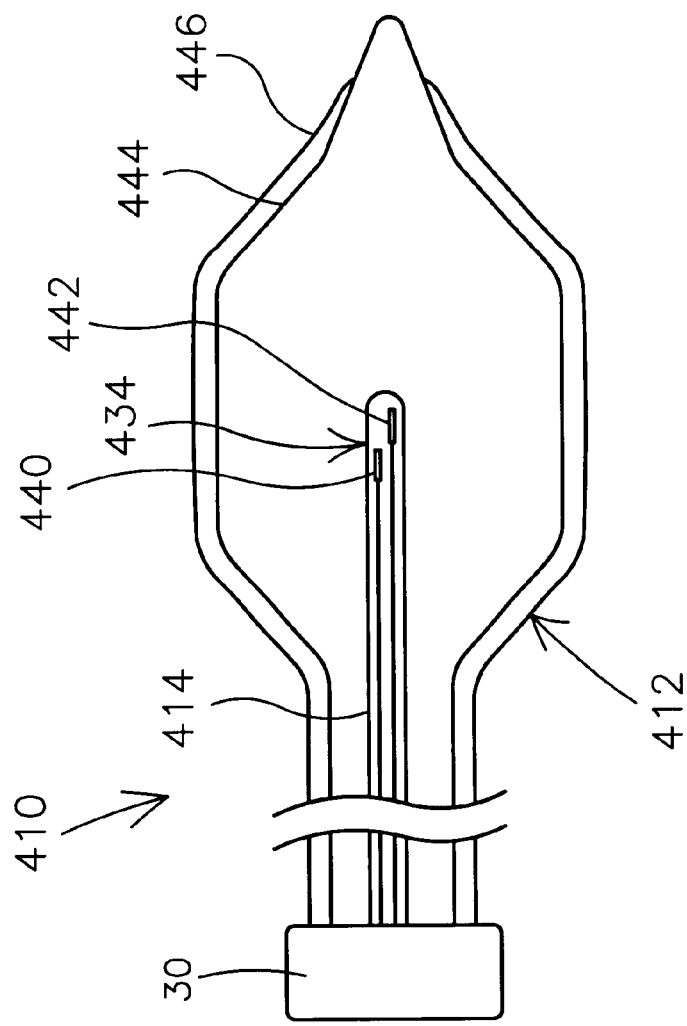
FIG. 8 is a fourth alternate embodiment of a cryo therapy apparatus.

The following description should be read with reference to the drawings wherein like reference numerals indicate like elements throughout the several views. The detailed description and drawings represent select embodiments and are not intended to be limiting.

FIG. 1 is a plan overview of a temperature monitoring device 10 for use with a cryo therapy apparatus 12 according to an embodiment of the invention. Temperature monitoring device 10 may include a tubular member 14 having a temperature monitoring member 20 coupled thereto. Temperature monitoring member 20 may be used to measure temperature while performing a medical procedure, for example cryo therapy, cryo balloon therapy, or cryoplasty.

Tubular member 14 includes a proximal end 16 and a distal end 18. Tubular member 14 may be coupled to cryo therapy apparatus 12, for example along the length or proximate an external surface of cryo therapy apparatus 12. Tubular member 14 may be comprised of materials including, but not limited to, metals, stainless steel, nickel alloys, nickel-titanium alloys, thermoplastics, high performance engineering resins, fluorinated ethylene propylene (FEP), polymer, polyethylene (PE), polypropylene (PP), polyvinylchloride (PVC), polyurethane, polytetrafluoroethylene (PTFE), polyether-ether ketone (PEEK), polyimide, polyamide, polyphenylene sulfide (PPS), polyphenylene oxide (PPO), polysufone, nylon, perfluoro (propyl vinyl ether) (PFA), combinations thereof, or other suitable materials.

Cryo therapy apparatus 12 is substantially similar to analogous devices (cryo therapy apparatuses, cryoplasty catheters, etc.) disclosed within U.S. Pat. No. 5,868,735 to Lafontaine and U.S. patent application Ser. No. 09/849,892 to Lafontaine, the entire disclosures of which are hereby incorporated by reference. Briefly, cryo therapy apparatus 12 may include a shaft with a cryoplasty device (e.g., a cryoplasty balloon) disposed at a distal end thereof. The shaft may include an inflation tube, a drain tube, and may further comprise an outer sheath defining an annular lumen between the outer sheath and the shaft. The annular lumen may be sealed such that a vacuum may be maintained therein. The cryoplasty device may include a single balloon or multiple balloons (i.e., a first balloon within a second balloon).

In use, coolant may pass through the inflation lumen into the cryoplasty device. The cryoplasty device may then be used for heat transfer with an area of interest. Coolant may be removed from the cryoplasty device through the drain tube following heat transfer.

Temperature monitoring member 20 may comprise a retractable thermocoupled needle 22 slidably disposed within a lumen 24 of tubular member 14. According to this embodiment, the inside diameter of tubular member 14 is sized appropriately for having temperature monitoring member 20 disposed within lumen 24. Thermocoupled retractable needle 22 is understood to include temperature sensing means that measure temperature in a manner that is quantifiable by a clinician. Alternatively, retractable needle 22 may include a temperature sensor coupled thereto. Retractable needle 22 may include a sharpened distal point 26 and at least one marker band 28. Distal point 26 may be adapted to penetrate and/or cut into tissue during a medical procedure.

From FIG. 1 it can be appreciated that temperature monitoring member 20 (and others described below) have a length along the longitudinal axis and extends away from cryo therapy apparatus 12 along the longitudinal axis. Moreover, an angle may be defined between temperature monitoring member 20 and cryo therapy apparatus 12. This angle may be about 90°, acute, or obtuse. It can also be seen in FIG. 1 that the length of temperature monitoring member 20 that extends from cryo therapy apparatus is greater than its width (measured along the axis perpendicular to the longitudinal axis).

Marker band 24 may produce a relatively bright image on a fluoroscopy screen during a medical procedure. This relatively bright image aids the user of marker band 24 in determining the location of temperature monitoring member 20. Marker band 24 may comprise a number of radiopaque materials including, but not limited to, gold, platinum, and plastic material loaded with a radiopaque filler. Temperature monitoring member 20 may further comprise additional marker bands or may comprise a marker band disposed at a different location. For example, marker band 24 may comprise a first marker band (e.g., marker band 24) a fixed distance from distal point 22 of temperature monitoring member 20. A second marker band may be disposed on temperature monitoring member 20 proximally a distance that is approximately equal to the distance the first marker band is from distal point 22.

Proximal end 16 of tubular member 14 may be connected to a manifold 30. Manifold 30 comprises means for controlling temperature monitoring member 20. More specifically, manifold 30 may comprise means for quantifying temperature as measured by, for example, thermocoupled needle 20. Means for quantifying temperature may include an analog temperature reading or display, a digital temperature reading or display, a connector for coupling to a computerized system for measuring temperature, a computerized system for processing other data, and combinations thereof.

In use, temperature monitoring device 10 may be advanced to an area of interest. The area of interest may be, for example, an artery including the pulmonary artery, a vein including the pulmonary vein, a blood vessel, the heart, trabeculae within the heart, a body organ, or other areas where cryoplasty may prove beneficial. Cryo therapy apparatus 12 may be used to cool the area of interest while temperature monitoring member 20 may be used to quantify temperature by inserting distal point 26 into tissue at the area of interest. In an embodiment, distal point 26 may contact the surface of the tissue at the area of interest or it may penetrate and/or cut into the tissue to measure temperature below the surface. Marker band 28 may be used to determine the location of distal point 26 during heat transfer. Accurately determining the location of distal point 26 may allow more precise cooling and prevent possible tissue damage due to over-cooling. Alternatively, the needles may have pre-determined depth marker band/stops which allow tissue penetration to a fixed depth such as 1–3 mm, etc.

FIG. 2 is a plan view of an alternate temperature monitoring device 110 according to an embodiment of the invention. Temperature monitoring device 110 is substantially similar to temperature monitoring device 10 except that temperature monitoring member 120 comprises an infrared or optic sensor 132. Element 118 is an extension of the tubular member 114 that is directed away from the cryo therapy apparatus and to which the temperature monitoring member 120 is attached. At least a portion of infrared or optic sensor 132 may be disposed within a lumen of tubular member 114, i.e., the equivalent of lumen 24 of tubular member 14. Alternatively, infrared or optic sensor 132 may be disposed proximate distal end 218 of tubular member 214.

Temperature monitoring device 110 may be used to measure temperature at an area of interest by detecting infrared energy at the area of interest with infrared sensor 32. Quantification of infrared energy may comprise a measurement of heat and/or temperature. Manifold 30 comprises means for quantifying temperature. For example, manifold 30 may comprise means for quantifying infrared energy.

Cooling may result in the formation of ice or ice balls adjacent cryo therapy apparatus 12 and/or the treatment site. As a result, alternative temperature monitoring members may be used. For example, in order to monitor or otherwise visualize ice or ice ball formation, optical sensing may be used. Optic sensing may be looking at the ice ball visually by color change or appearance of ice. Other methods may be used as described herein to monitor ice formation as well as methods known to those in the art.

FIG. 3 and FIG. 4 depict a plan overview of arrangements of tubular members 14 taken through section 3/4—3/4 of FIG. 1 and depicting additional tubular members 14. More than one tubular member 14 may be disposed about cryo therapy apparatus 12 in an array. Four tubular members 14 may be disposed about cryo therapy apparatus 12 in a quartet array as shown in FIG. 3. Similarly, FIG. 4 depicts eight tubular members 14, evenly spaced between, and disposed about cryo therapy apparatus 12 in an octet array. Although FIG. 3 and FIG. 4 depict arrangements of tubular member 14, it should be understood that any of the tubular members, temperature monitoring devices, and analogous structures disclosed herein may be substituted without departing from the spirit of the invention.

FIG. 5 is a plan view of an alternate temperature monitoring device 210 according to an embodiment of the invention. Temperature monitoring device 210 is substantially similar to temperature monitoring device 10 except that temperature monitoring member 220 comprises an ultrasound transmitter 234. Similar to what is disclosed above, at least a portion of ultrasound transmitter 234 may be disposed within a lumen of tubular member 214 or ultrasound transmitter 234 may be disposed at distal end 218 of tubular member 214.

Temperature monitoring device 210 may be used to measure temperature at an area of interest by transmitting ultrasound energy from ultrasound transmitter 234. Manifold 30 may comprise means for quantifying temperature including means for accumulating ultrasound images, ultrasound energy, and other ultrasound data. Analysis of ultrasound images, ultrasound energy, and other ultrasound data may provide an indirect measurement of temperature. For example, an ultrasound image may be used to view a phase change within the area of interest. The phase change may indicate a quantifiable level of cooling.

FIG. 6 is a detailed view of a tubular members 214 taken through line 6—6 of FIG. 5 and depicting addition tubular members 214. In an embodiment, tubular members 214 may be disposed about cryo therapy apparatus 12 in an array. In an exemplary embodiment, the array may be a circular array. The circular array may enable a user to more precisely measure temperature and determine the location of temperature monitoring device 210. In addition, tubular members 214 may be arranged in a quartet or octet array as disclosed above, and tubular members 14 and 114 may also be arranged in a circular array.

FIG. 7 is a plan view of an alternate temperature monitoring device 310 according to an embodiment of the invention. Temperature monitoring device 310 is substantially similar to temperature monitoring device 10 with a number of refinements described below.

Tubular member 314 comprises a sheath that, encircles cryo therapy apparatus 12. Temperature monitoring member 320 comprises a stent 36 disposed at distal end 318 of tubular member 314. Stent 36 may further comprise a plurality of thermal spikes 38. Stent 36 is comprised of a shape memory alloy (e.g., nickel-titanium alloy). Alternatively, stent 36 may be comprised of materials similar to those listed above including metals and polymers.

Thermal spikes 38 may be capable of measuring temperature at an area of interest. According to this embodiment, thermal spikes 38 may be coupled to manifold 30 such that a user may quantify temperature. Manifold 30 may comprise means for quantifying temperature including those listed above.

In addition, thermal spikes 38 may be used to facilitate heat transfer to an area of interest. For example, trabeculae within the heart may not allow cryo therapy apparatus 12 to evenly cool the heart. The result may be uneven or incomplete heat transfer. Thermal spikes 38 may be capable of reaching, contacting, and penetrating surfaces of an area of interest. For example, thermal spikes 38 may be capable of contacting trabeculae within the heart and may, thus, facilitate heat transfer to these areas.

In an embodiment, stent 36 may be collapsed at body temperature and be expanded when cooled. A collapsed state at body temperature will minimize the outside diameter of stent 36, which may facilitate delivery of temperature monitoring device 310 to an area of interest. Cooling, for example cooling initiated by cryo therapy apparatus 12, may expand stent 36 in order to move thermal spikes 38 proximate the area of interest.

FIG. 8 illustrates another alternative temperature monitoring device 410. Device 410 includes cryo therapy apparatus 412 coupled to manifold 30 essentially as described above. In addition, tubular member 414 may be coupled to cryo therapy apparatus 412. For example, tubular member 414 may be disposed at least partially within cryo therapy apparatus 12 or within the shaft portion of cryo therapy apparatus 12. When disposed within cryo therapy apparatus 12, tubular member 414 may be substantially coaxial with or proximate an interior wall of apparatus 12.

Temperature monitoring member 420 may be disposed within tubular member 441 and may extend into cryo therapy apparatus 12. In an alternative embodiment, temperature monitoring member 420 may be disposed within cryo therapy apparatus 12 without the use of tubular member 441. For example, temperature monitoring member 420 may be disposed within the shaft of cryo therapy apparatus 12.

Temperature monitoring member 420 includes an optical imaging apparatus 434 including an emitter 440 and a detector 442. Emitter 440 is adapted and configured to emit energy (e.g., light, infrared energy, ultrasonic energy, etc.) from within cryo therapy apparatus. Detector 442 is adapted to collect data by detecting energy. A number of different arrangements of emitters and/or detectors may be used without departing from the spirit of the invention.

Cryo therapy apparatus 412 is essentially the same in form and function as cryo therapy apparatus 12 but further includes an inner cooling chamber 444 and an outer cooling chamber 446. A dual-chamber cooling apparatus (such as apparatus 412) may provide additional safety or cooling advantages. For example, outer cooling chamber 446 may prevent loss of coolant into the body if inner cooling chamber 444 failed. It can be appreciated that the dual chamber cooling apparatus 412 can be substituted into any of the other embodiments described herein.

Numerous advantages of the invention covered by this document have been set forth in the foregoing description. It will be understood, however, that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A temperature monitoring device for minimally invasive medical treatment, comprising:
   a cryo therapy apparatus having a cooling chamber;
   a plurality of tubular members coupled to the cryo therapy apparatus, the tubular members each coupled to a temperature monitoring member and arranged in an array; and wherein the temperature monitoring member can measure the temperature at an area of interest while the cryoplasty device cools the area of interest.

2. The temperature monitoring device according to claim 1, wherein the tubular member further comprises a proximal end, a distal end, and a lumen extending therethrough.

3. The temperature monitoring device according to claim 2, wherein the temperature monitoring member comprises a retractable needle slidably disposed within the lumen of the tubular member.

4. The temperature monitoring device according to claim 3, wherein the retractable needle further comprises a marker band.

5. The temperature monitoring device according to claim 1, wherein the temperature monitoring member comprises an infrared sensor.

6. The temperature monitoring device according to claim 1, wherein the temperature monitoring member comprises an ultrasound transmitter.

7. The temperature monitoring device according to claim 1, wherein the temperature monitoring members are arranged in a quartet array.

8. The temperature monitoring device according to claim 1, wherein the temperature monitoring members are arranged in an octet array.

9. The temperature monitoring device according to claim 1, wherein the temperature monitoring members are arranged in a circular array.

10. The temperature monitoring device according to claim 1, wherein the temperature monitoring member an expandable stent having a plurality of thermal spikes.

11. The temperature monitoring device according to claim 1, wherein the stent comprises nickel-titanium alloy.

12. A temperature monitoring device for use in minimally invasive medical treatment, comprising:
   a cryo therapy, apparatus having a cryo therapy chamber;
   a tubular member coupled to the cryo therapy apparatus; and
   a temperature monitoring member attached to an extension directed away from the cryo therapy apparatus and coupled to the tubular member, the temperature monitoring member having a length extending from the cryo therapy apparatus along a longitudinal axis and a width; and
   wherein the length of the temperature monitoring member extending away from the cryo therapy apparatus along the longitudinal axis is larger than the width.

13. The temperature monitoring device in accordance with claim 12, wherein the temperature monitoring member extends from the cryo therapy apparatus at an angle.

14. The temperature monitoring device in accordance with claim 13, wherein the angle is about 90°.

15. The temperature monitoring device in accordance with claim 13, wherein the angle is acute.

16. The temperature monitoring device in accordance with claim 13, wherein the angle is obtuse.

17. A temperature monitoring device for minimally invasive medical treatment, comprising:
   a cryo therapy apparatus;
   a tubular member coupled to the cryo therapy apparatus; and
   a temperature monitoring member coupled to the tubular member and comprising a retractable needle slidably disposed within the lumen of the tubular member.

18. The temperature monitoring device according to claim 17, wherein the retractable needle further comprises a marker band.

19. A temperature monitoring device for minimally invasive medical treatment, comprising:
   a cryo therapy apparatus;
   a tubular member coupled to the cryo therapy apparatus; and
   a temperature monitoring member coupled to the tubular member, wherein the temperature monitoring member comprises an ultrasound transmitter.

20. A temperature monitoring device for minimally invasive medical treatment, comprising:
   a cryo therapy apparatus;
   a tubular member coupled to the cryo therapy apparatus; and
   a temperature monitoring member coupled to the tubular member wherein the temperature monitoring member comprises an expandable stent having a plurality of thermal spikes.

21. The temperature monitoring device according to claim 20, wherein the stent comprises nickel-titanium alloy.

* * * * *

UNITED STATES PATENT AND TRADEMARK OFFICE
CERTIFICATE OF CORRECTION

PATENT NO.   : 6,709,431 B2
DATED        : March 23, 2004
INVENTOR(S)  : Daniel M. LaFontaine It is certified that error appears in the above-identified patent and that said Letters Patent is hereby corrected as shown below:

Column 7,
Line 30, after "member" please insert -- comprises --;
Line 33, please delete "1" and insert -- 10 -- therefor;
Line 36, after "therapy please delete ",";

Column 8,
Line 30, after "member" please delete ",".

Signed and Sealed this

Sixteenth Day of November, 2004

JON W. DUDAS
*Director of the United States Patent and Trademark Office*